United States Patent [19]

Mori et al.

[11] 4,409,238
[45] Oct. 11, 1983

[54] INSECTICIDES AND INSECTICIDAL COMPOSITIONS

[75] Inventors: Fumio Mori, Kurashiki; Yoshiaki Omura, Okayama, both of Japan

[73] Assignee: Kuraray Co., Ltd., Kurashiki, Japan

[21] Appl. No.: 107,390

[22] Filed: Dec. 26, 1979

Related U.S. Application Data

[63] Continuation of Ser. No. 885,380, Mar. 10, 1979.

[30] Foreign Application Priority Data

| | | |
|---|---|---|
| Mar. 11, 1977 [JP] | Japan | 52-27510 |
| Mar. 23, 1977 [JP] | Japan | 52-32863 |
| Apr. 5, 1977 [JP] | Japan | 52-39237 |
| Apr. 11, 1977 [JP] | Japan | 52-41813 |

[51] Int. Cl.³ .................. A01N 9/20; A01N 9/24; C07C 69/65; C07C 121/75
[52] U.S. Cl. .................. 424/304; 260/465 D; 260/544 V; 424/314; 560/219; 562/598
[58] Field of Search .................. 424/304, 314

[56] References Cited

U.S. PATENT DOCUMENTS

| | | | |
|---|---|---|---|
| 3,996,244 | 12/1976 | Fujimoto et al. | 424/275 |
| 4,042,710 | 8/1977 | Bull et al. | 260/465 D |
| 4,058,622 | 11/1977 | Fujimoto et al. | 424/314 |
| 4,062,968 | 12/1977 | Fujimoto et al. | 424/275 |
| 4,161,536 | 7/1979 | Drabek et al. | 424/314 |
| 4,265,819 | 5/1981 | Lantsch | 424/314 |

*Primary Examiner*—Dale R. Ore
*Attorney, Agent, or Firm*—Burns, Doane, Swecker & Mathis

[57] ABSTRACT

Novel insecticidal compositions are comprised of an active isovalerate having the structural formula:

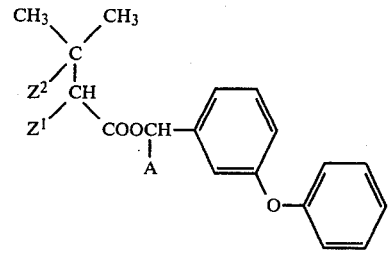

wherein $Z^1$ is hydrogen,

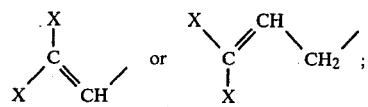

$Z^2$ is either

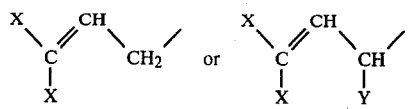

when $Z^1$ is hydrogen, or hydrogen when $Z^1$ is either

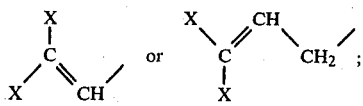

A, when $Z^1$ is

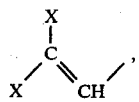

is cyano or ethynyl or, when $Z^1$ is other than

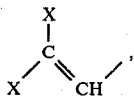

is hydrogen, cyano or ethynyl; X and Y which may be the same or different are chlorine or bromine.

53 Claims, No Drawings

INSECTICIDES AND INSECTICIDAL COMPOSITIONS

This is a continuation of application Ser. No. 885,380, filed Mar. 10, 1979.

BACKGROUND OF THE INVENTION

1. Field of the Invention

The present invention relates to certain novel insecticides and to novel insecticidal compositions comprising, as the active ingredient thereof, an isovaleric acid ester bearing a substituent group in the α- or β-position, said isovaleric acid ester having the structural formula [I]:

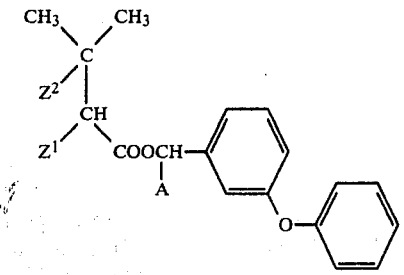

wherein $Z^1$ is hydrogen,

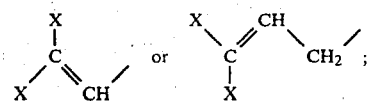

$Z^2$ is either

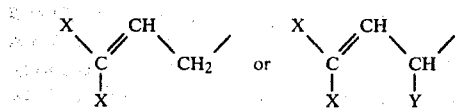

when $Z^1$ is hydrogen, or hydrogen when $Z^1$ is either

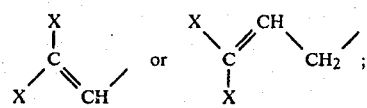

A, when $Z^1$ is

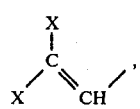

is cyano or ethynyl or, when $Z^1$ is other than

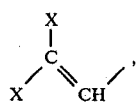

is hydrogen, cyano or ethynyl; X and Y which may be the same or different are chlorine or bromine.

The isovaleric acid ester substituted in the α- or β-position as represented by the above structural formula [I] comprises the four types of substituted isovaleric acid esters which are designated by the following structural formulae [I-A], [I-B], [I-C] and [I-D], respectively:

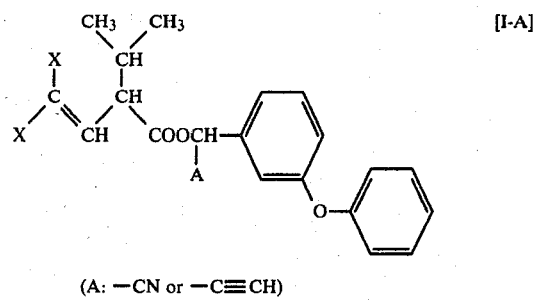

(A: —CN or —C≡CH)

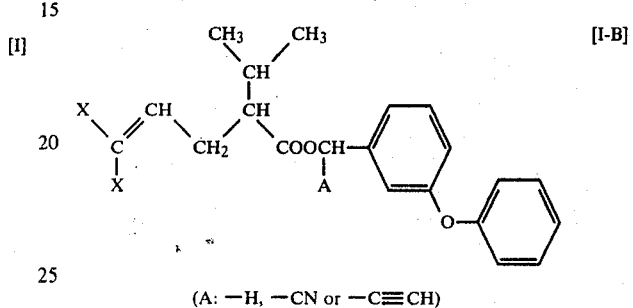

(A: —H, —CN or —C≡CH)

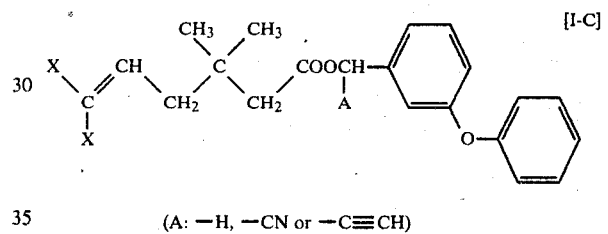

(A: —H, —CN or —C≡CH)

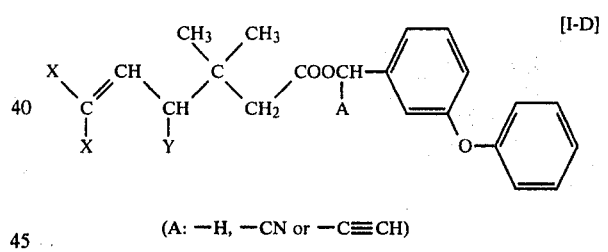

(A: —H, —CN or —C≡CH)

The compounds [I-A], [I-B] and [I-C] are the novel compounds according to the invention.

2. Description of the Prior Art

Since the discovery of BHC and DDT, there has been great development of a wealth of different insecticides containing, as the active ingredient thereof, a variety of organophosphorus compounds, carbamates, chlorinated organic compounds, and many others, for farming and gardening applications, and the use of such insecticides has resulted in marked increases in crop yields, thus enabling a stabilized supply of crops without depending upon climatic conditions. However, this success has been more or less offset by the fact that such agricultural and horticultural insecticides not only have high toxicity to humans and domesticated animals, but also same display a great tendency towards environmental pollution. Thus, the chronic toxicity and accumulation of such poisons have become a major contemporary concern. Furthermore, in many geographical areas, agricultural pests such as green rice leafhoppers, plant hoppers, etc., have been acquiring resistance to the common pesticides comprising the organic phosphorus compounds or the carbamates and the development of substitutes for such chemicals today is a pressing need. Pyrethroid pesticides, such as allethrin, phthalthrin, resmethrin, furamethrin, pyrethrin, etc., which have heretofore been employed for the purpose of controlling household pests are not only low in toxicity to man and domestic animals, have excellent pesticidal activities and are fast-acting against noxious insects, but too are known for the fact that pests acquire resistance thereto only very rarely. However, because of their extremely low stability to light and their low residual activity, these compounds cannot be used as agricultural or horticultural pesticides to replace the organophosphorus or carbamate pesticides.

Under these circumstances, there have been certain developments in agricultural and horticultural pesticides which take advantage of the characteristics of pyrethroids, which characteristics are not possessed by the conventional agricultural pesticides.

Among the pesticides recently developed have been 3-phenoxybenzyl (+)-cis,trans-2,2-dimethyl-3-(2,2-dichlorovinyl)-cyclopropanecarboxylate [Permethrin, U.S. Pat. No. 4,024,163] which has the structural formula:

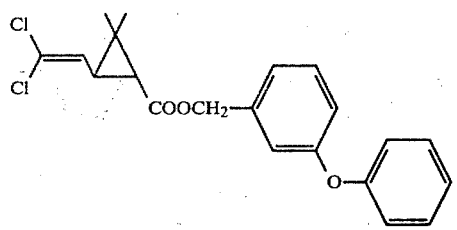

and α-cyano-3-phenoxybenzyl α-(4-chlorophenyl)isovalerate [Fenvalerate, U.S. Pat. No. 3,996,244] which has the structural formula:

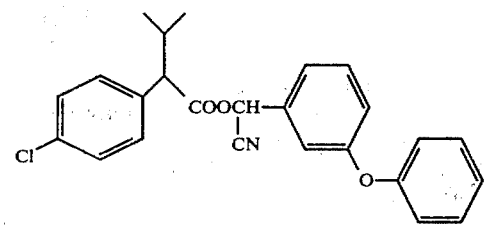

However, because of their high toxicity to fish, the applicability of these compounds is considerably restricted in geographical areas where, if used, they would contaminate the river water, etc.

Further, 3-phenoxybenzyl α-(2,2-dichlorovinyl)-isovalerate having the structural formula:

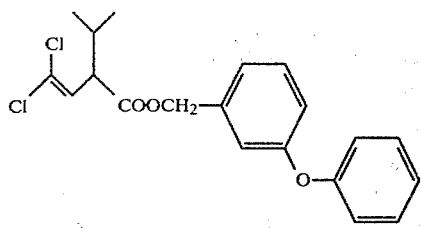

and α-(allyl or 3,3-dimethylallyl)isovaleric acid esters having the following structural formulae:

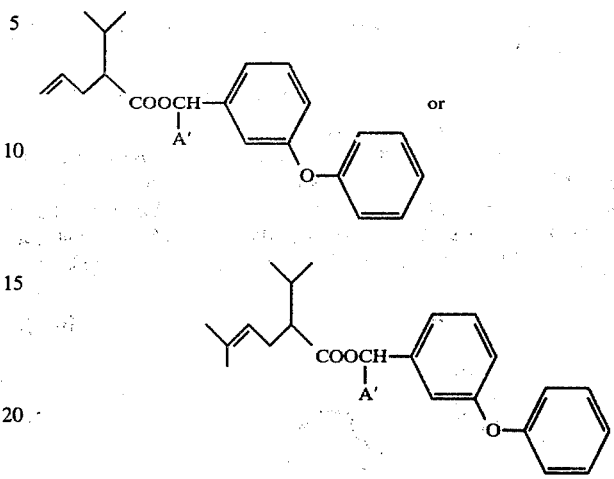

(wherein A' is hydrogen, alkynyl or cyano) are reported to have pesticidal activity against agricultural, horticultural and household pests [published, unexamined Japanese Patent Application No. 125723/1976 and U.S. Pat. No. 4,042,710]. However, none of such compounds displays a fully satisfactory pesticidal activity.

SUMMARY OF THE INVENTION

Accordingly, a primary object of the present invention is to provide a pesticide having the characteristic properties of pyrethroids and yet displaying a higher residual activity than the pyrethroids.

Briefly, there have now been prepared a number of isovaleric acid esters having a certain substituent in the α- or β-position, and which class of esters have been demonstrated to possess substantial pesticidal activity. More particularly, that class of α- or β-substituted isovaleric acid esters of the above structural formula [I] display markedly enhanced pesticidal activity as compared with the commonly employed allethrin, as well as excellent resistance to light and hydrolysis and excellent residual activity, with the bulk of such compounds exhibiting low toxicity to fish. The α- or β-substituted isovaleric acid esters of the structural formula [I] are not only pesticidally active against agricultural and horticultural pests injurious to rice paddy plants, dry-field crop plants, cotton plants, orchard trees, etc., such as green rice hoppers (*Nephotettia cincticeps* UHLER), plant hoppers (*Sogatella furcifera* HORVÁTH, *Nilaparvata lugens* STÅL, *Laodelphax striatellus* FALLÉN, etc.), rice stem borers (*Chilo suppressalis* WALKER), cabbage armyworm (*Mamestra brassica* LINNÉ), diamond-back moth (*Plutella maculipennis* CURTIS), owlet moths and underwings, common cabbage worm (*Pieris rapae crucivora* BOISDUVAL), Japanese giant silk moth (*Dictyoploca japonica* BUTLER), bean web worm (*Syllepte raralis* SCOPOLI), aphids, scale, mustard beetles (*Phaedon cochleariae* Fab.), boll weevils, pink bollworms (*Pectinophora gossypiella* Saund), tobacco budworms, mites, etc., but also display excellent pesticidal activity against household pests such as houseflies, mosquitoes, cockroaches (*Blatella germanica*), etc. It should be understood that where the α- or β-substituted isovaleric acid ester of structural formula [I] is a racemate, excellent activity will be obtained, even if the racemate is resolved.

DETAILED DESCRIPTION OF THE INVENTION

Among the α- or β-substituted isovaleric acid esters of structural formula [I], the α-substituted isovaleric acid esters of the structural formula [I-A] and the α-substituted isovaleric acid esters of structural formula [I-B] display particularly valuable pesticidal activity against the aforementioned variety of pests. The α-substituted isovaleric acid esters of structural formula [I-A] and the α-substituted isovaleric acid esters of structural formula [I-B] are much more lethal against agricultural and horticultural pests, such as green rice leafhoppers, than the known compound 3-phenoxybenzyl α-(2,2-dichlorovinyl)isovalerate, and, especially, α-(cyano or ethynyl)-3-phenoxybenzyl esters of α-(2,2-dihalogenovinyl or 3,3-dihalogenoallyl)isovaleric acids display markedly more lethal action against agricultural and horticultural pests.

Regarding the β-substituted isovaleric acid esters of structural formula [I-C] and the β-substituted isovaleric acid esters of structural formula [I-D], the 3-phenoxybenzyl esters display excellent pesticidal activity against household pests such as houseflies, while the α-(cyano or ethynyl)-3-phenoxybenzyl esters display a potent lethal action against agricultural and horticultural pests, such as green rice leafhoppers. The great bulk of the α- or β-substituted isovaleric acid esters are extremely low in toxicity to fish and applications therefor are promising as pesticides in localities where river water pollution and contamination are liable to take place. Thus, notwithstanding their varied pesticidal activities, the α- or β-substituted isovaleric acid esters of structural formula [I] are low in toxicity to man and animals, with most of the same being but sparingly toxic to fish; they are invariably highly resistant to light and hydrolysis; and they possess excellent residual activity.

Furthermore, the α- or β-substituted isovaleric acid esters of structural formula [I] are not only insecticidal, but also show promising repellent activity against mites and/or produce synergistic effects or results with other biologically active compounds. Thus, the compounds [I] can be made available at low cost as control agents against agricultural and horticultural insects, forest insects, insects injurious to harvested crops, household insects, and mites and other pests belonging to the following families: Tettigoniidae, Gryllidae, Gryllotalpidae, Blattidae, Reduviidae, Pyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae, Pulicidae, Tetranychidae, and Dermanyssidae.

The following is an exemplary list of certain desirable α- or β-substituted isovaleric acid esters of the structural formula [I] according to this invention:

| Compound No. | Structural formula |
|---|---|
| [1] | α-Cyano-3-phenoxybenzyl α-(2,2-dichlorovinyl) isovalerate |
| [2] | α-Ethynyl-3-phenoxybenzyl α-(2,2-dichlorovinyl) isovalerate |
| [3] | α-Cyano-3-phenoxybenzyl α-(2,2-dibromovinyl) isovalerate |
| [4] | α-Ethynyl-3-phenoxybenzyl α-(2,2-dibromovinyl) isovalerate |
| [5] | 3-Phenoxybenzyl α-(3,3-dichloroallyl) isovalerate |
| [6] | α-Cyano-3-phenoxybenzyl α-(3,3-dichloroallyl) isovalerate |

| Compound No. | Structural formula |
|---|---|
| [7] | α-Ethynyl-3-phenoxybenzyl α-(3,3-dichloroallyl)isovalerate |
| [8] | 3-Phenoxybenzyl α-(3,3-dibromoallyl)isovalerate |
| [9] | α-Cyano-3-phenoxybenzyl α-(3,3-dibromoallyl)isovalerate |
| [10] | α-Ethynyl-3-phenoxybenzyl α-(3,3-dibromoallyl)isovalerate |
| [11] | 3-Phenoxybenzyl β-(3,3-dichloroallyl)isovalerate |
| [12] | α-Cyano-3-phenoxybenzyl β-(3,3-dichloroallyl)isovalerate |
| [13] | α-Ethynyl-3-phenoxybenzyl β-(3,3-dichloroallyl)isovalerate |
| [14] | 3-Phenoxybenzyl β-(3,3-dibromoallyl)isovalerate |
| [15] | α-Cyano-3-phenoxybenzyl β-(3,3-dibromoallyl)isovalerate |
| [16] | α-Ethynyl-3-phenoxybenzyl β-(3,3-dibromoallyl)isovalerate |
| [17] | 3-Phenoxybenzyl β-(1,3,3-trichloroallyl)isovalerate |
| [18] | α-Cyano-3-phenoxybenzyl β-(1,3,3-trichloroallyl)isovalerate |
| [19] | α-Ethynyl-3-phenoxybenzyl β-(1,3,3-trichloroallyl)isovalerate |
| [20] | 3-Phenoxybenzyl β-(1-chloro-3,3-dibromoallyl)isovalerate |
| [21] | α-Cyano-3-phenoxybenzyl β-(1-chloro-3,3- |

-continued

| Compound No. | Structural formula |
|---|---|
| | dibromoallyl)isovalerate |
| [22] | α-Ethynyl-3-phenoxybenzyl β-(1-chloro-3,3-dibromoallyl)isovalerate |
| [23] | 3-Phenoxybenzyl β-(1-bromo-3,3-dichloroallyl)isovalerate |
| [24] | α-Cyano-3-phenoxybenzyl β-(1-bromo-3,3-dichloroallyl)isovalerate |
| [25] | α-Ethynyl-3-phenoxybenzyl β-(1-bromo-3,3-dichloroallyl)isovalerate |
| [26] | 3-Phenoxybenzyl 3-(1,3,3-tribromoallyl)isovalerate |
| [27] | α-Cyano-3-phenoxybenzyl β-(1,3,3-tribromoallyl)isovalerate |
| [28] | α-Ethynyl-3-phenoxybenzyl β-(1,3,3-tribromoallyl)isovalerate |

Among the α- or β-substituted isovaleric acid esters of structural formula [I], the α-substituted isovaleric acid esters of structural formula [I-A], the α-substituted isovaleric acid esters of structural formula [I-B] and the β-substituted isovaleric acid esters of structural formula [I-C] are novel compounds, and each can be easily synthesized via the following sequences (i) to (iii):

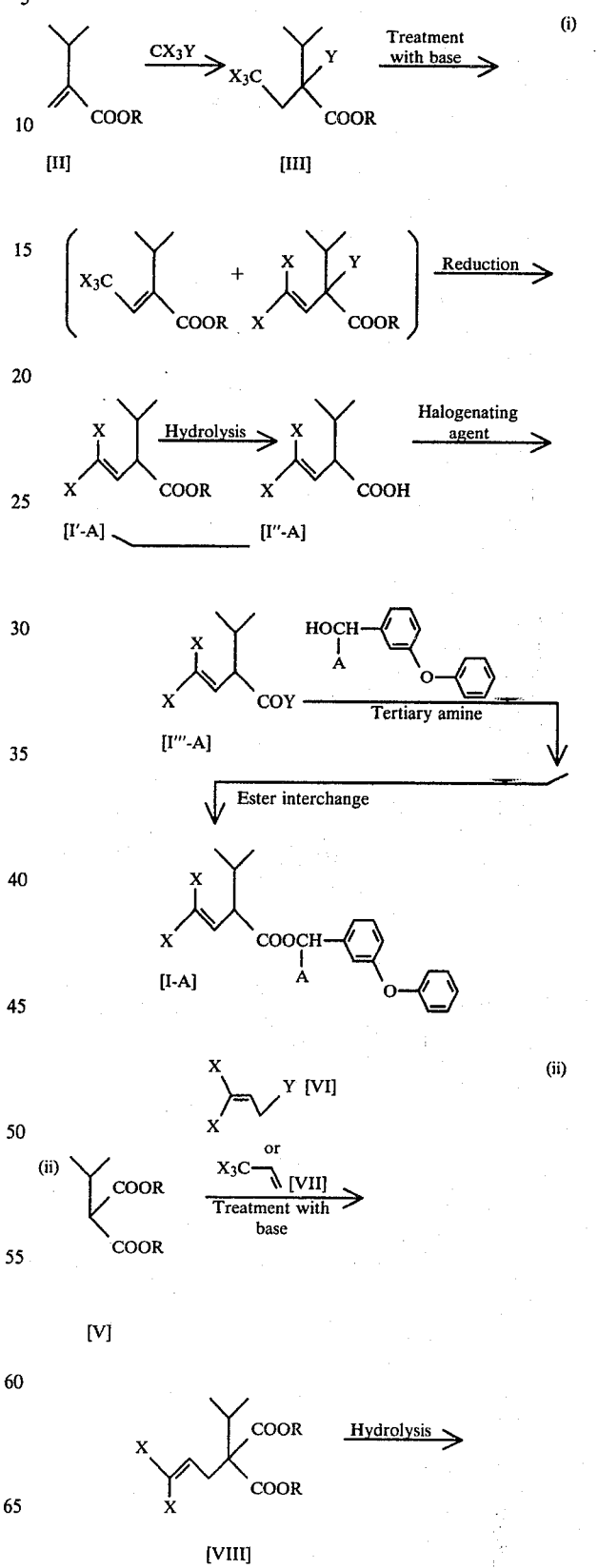

-continued

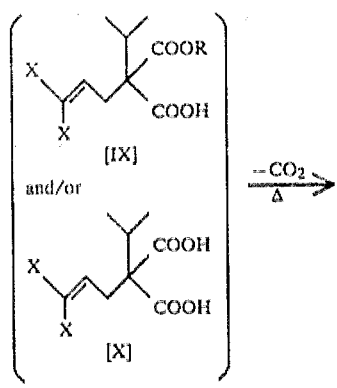

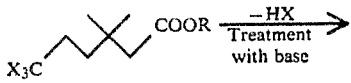

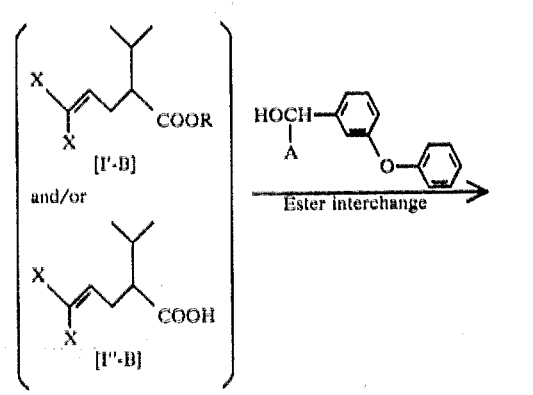

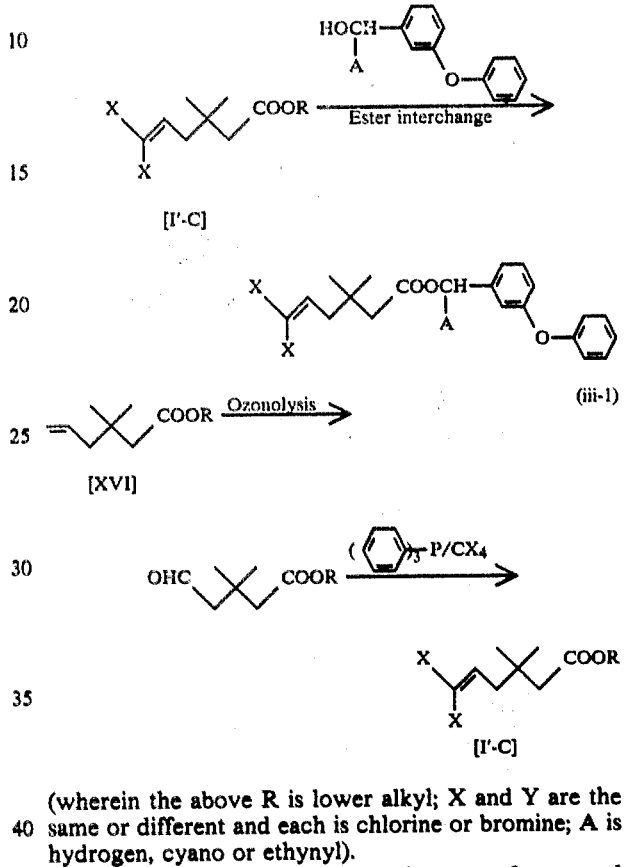

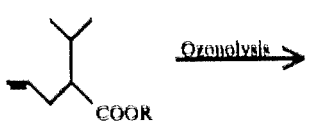

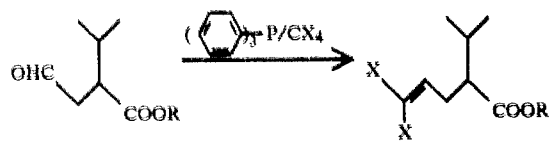

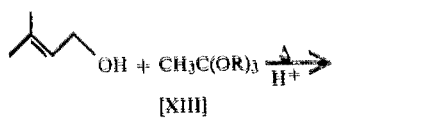

(wherein the above R is lower alkyl; X and Y are the same or different and each is chlorine or bromine; A is hydrogen, cyano or ethynyl).

Thus, α-substituted isovaleric acid esters of structural formula [I-A] are produced by the above process (i). First, a compound of structural formula [II] and a tetrahalogenomethane, e.g., tetrachloromethane (carbon tetrachloride), tetrabromomethane (carbon tetrabromide), or monobromotrichloromethane, are heated to 80°–150° C. in the presence of a radical initiator such as benzoyl peroxide (BPO), azobisisobutyronitrile (AIBN), acetyl peroxide or t-butyl perbenzoate to obtain a compound of structural formula [III]. Then, this compound of structural formula [III] is treated with a base such as 1,5-diazabicyclo[3,4,0]nonene-5 (DBN), 1,5-diazabicyclo[5,4,0]undecene-5(DBU), sodium ethoxide, potassium t-butoxide, sodium hydroxide or the like and the resultant product is reduced to a compound of structural formula [I'-A]. The above treatment with a base is desirably carried out in an inert organic solvent such as chloroform, tetrachloromethane, benzene, toluene, methanol, ethanol, tetrahydrofuran, n-hexane or the like at a temperature of about 0° C. to about 100° C. The reduction reaction is preferably carried out in an atmosphere of hydrogen gas and in the presence of a reduction catalyst, e.g., palladium-on-carbon, palladium-on-barium sulfate or palladium black, using a solvent such as methanol, ethanol or n-hexane at a temperature which may range from room temperature to 100° C. Then, the compound of structural formula

[I'-A] is hydrolyzed in a conventional manner to the free carboxylic acid [I"-A] which, in turn, is treated with a halogenating agent such as thionyl chloride, thionyl bromide, phosphorus trichloride, phosphorus tribromide, phosphorus oxychloride, phosphorus oxybromide or the like to obtain the corresponding carboxylic acid halide [I'''-A]. This carboxylic acid halide [I'''-A] is further reacted with an alcohol of structural formula [IV] in the presence of a tertiary amine such as pyridine or triethylamine. By the above procedure, there is obtained the α-substituted isovaleric acid ester of structural formula [I-A]. An α-substituted isovaleric acid ester of structural formula [I-A] may also be produced from a compound of structural formula [I'-A] or a free carboxylic acid of structural formula [I"-A] by several other alternative processes known per se, viz., (a) a transesterification process which comprises reacting a compound of structural formula [I'-A] directly with an alcohol of structural formula [IV], (b) an esterification reaction involving a dehydration condensation which comprises reacting a free carboxylic acid of structural formula [I"-A] with an alcohol [IV], (c) an esterification process in which a salt of free carboxylic acid [I"-A] with an alkali metal, silver or organic tertiary base is reacted with a sulfoxylate or halide of an alcohol [IV] or a quaternary ammonium salt thereof, and (d) an esterification reaction which comprises reacting the acid anhydride of a free carboxylic acid [I"-A] with an alcohol [IV].

The α-substituted isovaleric acid esters of structural formula [I-B] can be produced by the above process (ii). First, a lower alkyl ester of isopropylmalonic acid of structural formula [V] is reacted with a halogen compound of structural formula [VI] or [VII], such as 1,1-dichloro-3-bromo-1-propene, 1,1-dibromo-3-chloro-1-propene, 1,1,3-trichloro-1-propene, 1,1,3-tribromo-1-propene, 3,3,3-trichloro-1-propene, 3,3,3-tribromo-1-propene, or the like, in the presence of a basic reagent at a temperature in the range of 0° to 100° C. to prepare a compound of structural formula [VIII]. As examples of said basic reagent, there are mentioned sodium methoxide, sodium ethoxide, sodium t-butoxide, potassium t-butoxide, sodium hydride, sodium amide, butyllithium, sodium hydroxide, potassium hydroxide, sodium carbonate, 1,4-diazabicyclo[5,4,0]undecene-5[DBU] and 1,5-diazabicyclo[3,4,0]nonene-5(DBN). Then, the compound of structural formula [VIII] is treated with potassium hydroxide, sodium hydroxide or the like and, then, neutralized with acid. By this hydrolytic treatment which is conventional, per se, the monoester of structural formula [IX] and/or dicarboxylic acid of structural formula [X] can be obtained. Thus, depending on the conditions of hydrolysis, for example, the relative amount of potassium hydroxide, sodium hydroxide, or the like, based on the compound of structural formula [VIII], the time and temperature of reaction, etc., either a compound of structural formula [IX] or a compound of structural formula [X] or a mixture of [IX] and [X] is obtained. The monoester of structural formula [IX] and/or the dicarboxylic acid of structural formula [X] is subjected to decarboxylation reaction by heating it at a temperature in the range of 120° to 250° C., whereby a compound of structural formula [I'-B] and/or a free carboxylic acid of structural formula [I"-B] are obtained. Where the compound of structural formula [I'-B] and the free carboxylic acid of structural formula [I"-B] are obtained as a mixture, these compounds may be separated from each other by distillation or like procedure or, alternatively, the mixture may be hydrolyzed so as to convert the compound of structural formula [I'-B] to the free carboxylic acid [I"-B]. The compound of structural formula [I'-B] can also be easily produced by the process [ii-1] as well. Thus, ozone gas is bubbled into a solution of the γ,δ-unsaturated carboxylic acid ester of structural formula [XI] in a solvent such as methanol or n-hexane at −20° C. to −10° C., whereby an aldehyde compound of structural formula [XII] is obtained. The aldehyde compound of structural formula [XII] is subjected to the so-called Wittig reaction, that is to say, reacted with the phospholane as formed from triphenylphosphine and carbon tetrahalide [U.S. Pat. No. 4,021,163], whereby a compound of structural formula [I'-B] can be easily obtained. The carbon tetrahalide mentioned above is preferably carbon tetrachloride or carbon tetrabromide. The Wittig reaction is expediently accomplished in the solvent used in the preparation of phospholane, although it may be conducted in any other solvent which does not interfere with the Wittig reaction, such as methylene chloride, benzene or the like. The α-substituted isovaleric acid ester of structural formula [I-B] can be obtained by subjecting either the compound of structural formula [I'-B] or the free carboxylic acid of structural formula [I"-B] to an ester interchange reaction similar to the above-mentioned process (i).

The β-substituted isovaleric acid ester of structural formula [I-C] can be produced by the above process (iii). Thus, initially, an orthocarboxylic acid ester [XIII] is permitted to react with 3-methyl-2-buten-1-ol in the presence of an acidic catalyst such as propionic acid, butyric acid, valeric acid, p-toluenesulfonic acid, phenol or hydroquinone at a temperature in the range of 120° to 160° C. By this reaction procedure there is obtained the γ,δ-unsaturated carboxylic acid ester [XIV] [published, unexamined Japanese Patent Applications No. 65710/1976 and No. 86410/1976]. Then, this γ,δ-unsaturated carboxylic acid ester [XIV] is reacted with chloroform in the presence of a catalyst, for example, in the presence of a radical initiator such as azobisisobutyronitrile (AIBN), benzoyl peroxide (BPO), acetyl peroxide, di-t-butyl peroxide, t-butyl peracetate, t-butyl perbenzoate, t-butyl perphthalate, t-butyl hydroperoxide, or the like, at a temperature in the range of 60° to 150° C. whereby the addition compound [XV] is obtained. This addition compound [XV] is next treated with a base such as sodium methoxide, sodium ethoxide, sodium t-butoxide, potassium t-butoxide, sodium isoamylate, 1,5-diazabicyclo[5,4,0]undecene-5 (DBU), 1,5-diazabicyclo[3,4,0]nonene05 (DBN), sodium hydroxide, potassium hydroxide, sodium amide, sodium hydride, butyllithium, or the like, at a temperature in the range of −70° to +150° C., whereby a compound of structural formula [I'-C] is obtained. The compound of structural formula [I'-C] can also be produced by the method (iii-1). This process can be effected by the same procedure as that of process (ii-1) except that the compound of structural formula [XVI] is used in lieu of the compound of structural formula [XI]. By an ester interchange reaction of the compound of structural formula [I'-C] in a manner analogous to that of the above process (i), there can be obtained the β-substituted isovaleric acid ester of structural formula [I-C].

The β-substituted isovaleric acid ester represented by the structural formula [I-D] is known only as an intermediate in the synthesis of 2,2-dimethyl-3-(2,2-dichlorovinyl)-cyclopropanecarboxylic acid which is the acid moiety of the aforementioned permethrin [published, unexamined Japanese Patent Applications No. 98248/1976, No. 125251/1976 and No. 125252/1976]. The β-substituted isovaleric acid ester of structural formula [I-D] can be easily produced, for example, by the following process (iv):

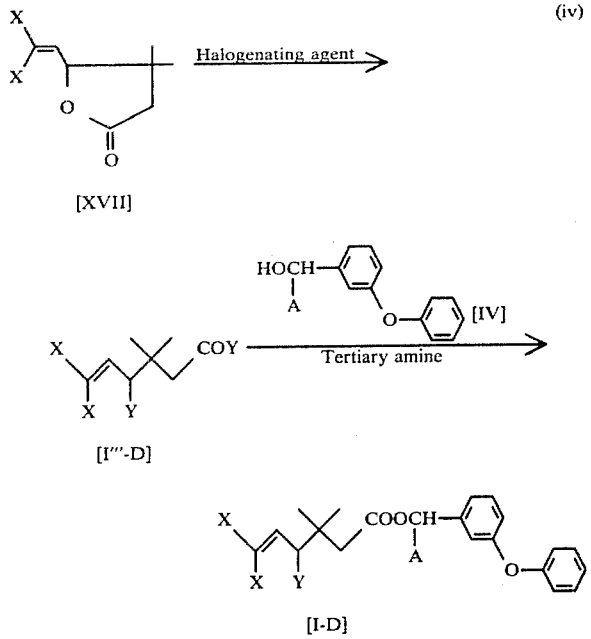

[XVII]

[I'''-D]

[I-D]

(wherein X and Y are the same or different and each is chlorine or bromine, A is hydrogen, cyano or ethynyl).

Thus, initially, a γ-lactone of structural formula [XVII] is reacted with a halogenating agent to prepare a carboxylic acid halide of structural formula [I'''-D]. When the halogenating agent is thionyl chloride, phosphorous pentachloride or phosphorus oxychloride, there is obtained a compound of structural formula [I'''-D] wherein Y is chlorine, while a compound of structural formula [I'''-D] in which Y is bromine is obtained when thionyl bromide or phosphorus pentabromide, for instance, is employed as said halogenating agent [published, unexamined Japanese Patent Application No. 12160/1977]. The carboxylic acid halide of structural formula [I'''-D] can also be produced by that method comprising reacting a γ-lactone of structural formula [XVII] with a thionyl halide in the presence of a Lewis acid catalyst, e.g., zinc chloride, tin tetrachloride, or the like, and a hydrogen halide. Then, in an inert solvent, the carboxylic acid halide of structural formula [I'''-D] is reacted with an alcohol of structural formula [IV] in the presence of a tertiary amine, such as pyridine or triethylamine, whereby a β-substituted isovaleric acid ester of structural formula [I-D] is easily obtained [published, unexamined Japanese Patent Application No. 125150/1977].

The α- or β-substituted isovaleric acid ester of general formula [I] (hereinafter referred to as the "active" compound) can be used in the form of conventional formulations, such as solutions, emulsifiable concentrates, wettable powders, suspensions, dusts, granules, microfine granules, powders, coatings, aerosols, mosquito incense coils, fumigants, slow-acting or delayed release fumigants, electric mosquito incense mats, capsules, and so forth. These formulations may be prepared by conventional procedures, for example, by admixing the active compound with a volume builder, such as a liquid, solid or liquefied gas diluent or carrier (optionally with a surfactant, i.e., an emulsifier, and/or a dispersing agent, and/or a foaming agent). Where water is employed as the volume builder, an organic solvent may be employed as a co-solvent.

Suitable liquid diluents usually include aromatic hydrocarbons, such as xylene, toluene, benzene, alkylnaphthalene, etc.; chlorinated aromatic or aliphatic hydrocarbons, such as chlorobenzene, chloroethylene, methylene chloride, etc.; aliphatic or alicyclic hydrocarbons, such as cyclohexane, paraffin (e.g., mineral oil distillate); alcohols, such as butanol, glycol and its ether and ester; ketones, such as acetone, methyl ethyl ketone, methyl isobutyl ketone, cyclohexanone, etc.; highly polar solvents, such as dimethylformamide, dimethylsulfoxide, acetonitrile, etc.; and water.

By "liquefied gas diluent" there is intended a liquid which is gaseous at normal temperature and pressure, such as aerosol propellants, e.g., dichlorodifluoromethane, trichlorofluoromethane, etc.

Preferred examples of said solid diluent or carrier are finely divided, naturally occurring minerals such as kaolin, clay, talc, chalk, quartz, attapulgite, montmorillonite, diatomaceous earth, etc.; and finely divided synthetic minerals such as alumina, silicates, etc.

As preferred examples of said emulsifiers and foaming agents there are mentioned nonionic and anionic emulsifying agents, such as polyoxyethylene-aliphatic carboxylic acid esters; polyoxyethylene-aliphatic alcohol ethers, such as alkyl aryl polyglycol ether; alkylsulfonates, alkylsulfates, arylsulfonates and albumin hydrolysate. Preferred examples of the dispersing agents include spent lignosulfite liquor and methyl-cellulose.

Adhesive agents, such as carboxymethyl-cellulose; powdery, granular or latex-type naturally occurring or synthetic high molecular weight compounds, such as gum Arabic, polyvinyl alcohol, polyvinyl acetate, etc., may be employed in the preparation of said formulations. In addition, colorants such an inorganic pigments, e.g., iron oxide, titanium oxide, etc.; and organic dyestuffs, e.g., alizarin dyes, azo dyes, phthalocyanine dyes, etc., too may be incorporated in the subject formulations.

The pesticidal activity of the active compound according to this invention can be further improved by the addition of synergists, such as N-octylbicycloheptene dicarboximide (trademark MGK-264), a mixture of N-octylbicycloheptene dicarboximide and alkyl aryl sulfonate (trademark MGK-5026), octachloro dipropyl ether, piperonyl butoxide, etc. The stability of the abovementioned active compound which is an active ingredient of these pesticidal formulations can be increased by the addition of an antioxidant of the phenol, amine or other type, such as 2,6-di-t-butyl-4-methylphenol (BHT), 2,6-di-t-butylphenol, etc.

Insecticidal compositions or formulations having yet further improved activity may be obtained by using the active compound of this invention in combination with other pesticides. Among such pesticides are chlorinated organic pesticides such as DDT, BHC, Methoxychlor, etc., carbamates such as 1-naphthyl N-methylcarbamate, 3,4-dimethylphenyl N-methylcarbamate, 3,5-dimethylphenyl N-methylcarbamate, 2-isopropoxyphenyl N-methylcarbamate, etc.; organophosphorus compounds such as O,O-dimethyl-O-(3-methyl-4-nitrophenyl)phosphorothioate, DDVP [O,O-dimethyl-O-

(2,2-dichlorovinyl)phosphate], diazinon, phenthion, O,O-dimethyl-O-4-cyanophenyl phosphorothionate, O,O-dimethyl-S-[α-(ethoxycarbonyl)benzyl]phosphorodithioate, 2-methoxy-4H-1,3,2-benzodioxaphosphorin-2-sulfide, O-ethyl-O-4-cyanophenyl phenylphosphonothionate, etc.; cyclopropanecarboxylic acid esters such as pyrethrin, allethrin, N-(3,4,5,6-tetrahydrophthalimido) methyl crysanthemate (tetramethrin), 5-benzyl-3-furylmethyl chrysanthemate (resmethrin), 5-propargylfurfuryl chrysanthemate (furamethrin), 5-propargyl-2-methyl-3-furylmethyl chrysanthemate (proparthrin), 3-phenoxybenzyl chrysanthemate (phenothrin), α-ethynyl-3-phenoxybenzyl chrysanthemate, 3-phenoxybenzyl 2,2-dimethyl-3-(2,2-dichlorovinyl)cyclopropanecarboxylate(permethrin), α-ethynyl-3-phenoxybenzyl 2,2-dimethyl-3-(2,2-dichlorovinyl) cyclopropanecarboxylate, α-cyano-3-phenoxybenzyl 2,2-dimethyl-3-(2,2-dichlorovinyl)cyclopropanecarboxylate, etc.; and substituted acetic acid esters such as α-cyano-3-phenoxybenzyl α-(4-chlorophenyl)isovalerate, α-ethynyl-3-phenoxybenzyl α-(4-chlorophenyl)isovalerate, etc.

In each formulation, the active compound is generally incorporated in an amount ranging from 0.01 to 95 weight percent, preferably from about 0.1 to 90 weight percent.

The active compound of this invention can be used in any of the aforementioned varied types of formulations or as further formulated into various application forms. The content of the active compound in such an application form may be varied over a broad range. The concentration of active compound in such an application form may range from 0.0000001 to 100 weight percent, preferably from about 0.001 to 10 weight percent.

The pesticides containing any of the active compounds according to this invention can be put to use by routine procedures suited to individual modes of application.

The following examples of synthesis, test examples, formulation examples and utility examples are further illustrative of this invention, and are nowise intended as limitative. In the formulation examples and utility examples, all parts are by weight. The compound numbers correspond to the α- or β-substituted isovaleric acid esters [1] to [28] of the structural formula [I] mentioned hereinbefore.

SYNTHESIS EXAMPLE 1

To a mixture of 4.4 g of ethyl α-isopropylacrylate and 40 g of monobromotrichloromethane was added 0.14 g of t-butyl perbenzoate and the entire mixture was heated at 120° C. for 12 hours. The reaction mixture was distilled to remove the low-boiling fraction and, then, further subjected to distillation under reduced pressure to recover 8.5 g of ethyl α-bromo-α-(2,2,2-trichloroethyl)isovalerate, b.p. 132°–136° C./0.8 mmHg (yield 81%).

In 20 g of chloroform were dissolved 6.0 g of the ethyl α-bromo-α-(2,2,2-trichloroethyl)isovalerate and, after the addition of 3.5 g of 1,5-diazabicyclo[5,4,0]undecene-5(DBU), the solution was stirred at room temperature for 2 hours. The reaction mixture was then diluted with diethyl ether, washed with water and dilute aqueous hydrogen chloride and dried over anhydrous magnesium sulfate. The low-boiling fraction was removed by distillation, whereupon 4.6 g of oily product were obtained. Based on its NMR spectrum and GC-mass spectrum, this product was identified to be ethyl α-isopropyl-β-trichloromethylacrylate containing a certain amount of ethyl α-bromo-α-(2,2-dichlorovinyl) isovalerate. In 50 ml of ethanol were dissolved 4.6 g of the oily product obtained above and, following the addition of 0.4 g of 5% palladium-on-carbon, the solution was stirred in an atmosphere of hydrogen gas at 55° C. for 6 hours. Thereafter, the reaction mixture was filtered to remove the catalyst and the ethanol was distilled off. By the above procedure there were obtained 3.9 g of ethyl α-(2,2-dichlorovinyl)isovalerate as an oil. Then, 3.9 g of this ethyl α-(2,2-dichlorovinyl)isovalerate were dissolved in 20 ml of ethanol and a solution of 2.0 g of sodium hydroxide in 10 ml of water was added to the above ethanol solution. The mixture was stirred at room temperature for 10 hours, at the end of which time the ethanol was distilled off. The residue was neutralized with aqueous hydrogen chloride and extracted with diethyl ether. The ethereal solution yielded 2.9 g of α-(2,2-dichlorovinyl)isovaleric acid having the following NMR spectrum [yield: 84% based on ethyl α-bromo-α-(2,2,2-trichloroethyl)isovalerate].

NMR spectrum (60 MHz) $\delta_{TMS}^{CCl_4}$: 0.97(d, J=7 Hz), 1.03(d, J=7 Hz) 6H; 1.83–2.36(m)1H; 3.23(d, J=10 Hz), 3.35(d, J=10 Hz)1H; 6.04(d, J=10 Hz)1H.

In 15 ml of dry benzene were dissolved 1.8 g of α-(2,2-dichlorovinyl)isovaleric acid, followed by the addition of 3.5 g of thionyl chloride. The mixture was refluxed for 5 hours and, then, distilled to remove the low-boiling fraction. By the above procedure there was obtained α-(2,2-dichlorovinyl)isovaleroyl chloride. This chloride was dissolved in 20 ml of benzene, and 2.0 g of α-ethynyl-3-phenoxybenzyl alcohol were added. This was followed by the addition of 2.9 g of pyridine and the mixture was stirred at room temperature for 8 hours. The resultant reaction mixture was diluted with diethyl ether, washed with water and dilute aqueous hydrogen chloride and dried over anhydrous magnesium sulfate. The low-boiling fraction was then distilled off and the residue was chromatographed on a column of silica gel (benzene/n-hexane=1:1 v/v). By the above procedure there were obtained 2.6 g of α-ethynyl-3-phenoxybenzyl α-(2,2-dichlorovinyl)isovalerate (compound [2]) having the following properties [yield: 71% based on α-(2,2-dichlorovinyl)isovaleric acid].

NMR spectrum (60 MHz) $\delta_{TMS}^{CDCl_3}$: 0.78–1.06(m)6H, 1.80–2.47(m)1H, 2.61(d, J=2 Hz)1H, 3.29 (dd, J=7 Hz & 10 Hz)1H, 6.00(d, J=10 Hz)1H, 6.44(d, J=2 Hz) 1H, 6.85–7.55(m)9H.

Elemental analysis (Calcd. in parentheses): C% 65.65(65.52) H% 5.09 (5.00).

SYNTHESIS EXAMPLE 2

In 20 ml of dry benzene were dissolved 2.0 g of α-(2,2-dichlorovinyl)isovaleric acid, followed by the addition of 6.0 g of thionyl chloride. The mixture was refluxed overnight. It was then distilled to remove the low-boiling fraction, whereby α-(2,2-dichlorovinyl)isovaleroyl chloride was obtained. This α-(2,2-dichlorovinyl)isovaleroyl chloride was dissolved in 25 ml of dry benzene, followed by the addition of 2.3 g of α-cyano-3-phenoxybenzyl alcohol and, then, 2.4 g of pyridine. The mixture was stirred at room temperature overnight. The resultant reaction mixture was diluted with diethyl ether, washed with water and dilute aqueous hydrogen chloride, dried over anhydrous magnesium sulfate and distilled to remove the low-boiling fraction. Column chromatography was carried out on the residue to obtain 3.2 g of α-cyano-3-phenoxybenzyl α-(2,2-dichlorovinyl)isovalerate (Compound [1]) which was shown to have the properties given below [yield: 78% based on α-(2,2-dichlorovinyl)isovaleric acid].

NMR spectrum (60 MHz) $\delta_{TMS}^{CDCl_3}$: 0.78–1.04(m)6H, 1.74–2.40(m)1H, 3.31(dd, J=7 Hz & 10 Hz)1H, 5.95(d, J=10 Hz)1H, 6.33(s)1H, 6.87–7.53(m)9H.

Elemental analysis (Calcd. in parentheses): C% 62.28(62.39) H% 4.70(4.74).

SYNTHESIS EXAMPLE 3

10.5 g of sodium hydride (ca. 50%) were washed with n-hexane and suspended in 430 g of benzene with stirring. To this suspension were added 36.8 of diethyl isopropylmalonate and the mixture was refluxed for about 40 minutes. The reaction mixture was then allowed to stand and cool for about 20 minutes, after which 37.9 g of 1,1-dichloro-3-bromo-1-propane were added in several increments. The mixture was then stirred under reflux for 1.5 hours. After cooling, the reaction mixture was washed with water and dilute hydrochloric acid, dried over anhydrous magnesium sulfate and distilled to remove the low-boiling fraction. The resultant oil was further distilled under reduced pressure to obtain 52.3 g of diethyl isopropyl-(3,3-dichloroallyl)malonate which was shown to have the following NMR spectrum [yield: 92% based on diethyl isopropylmalonate].

NMR spectrum (60 MHz) $\delta_{HMS}^{CCl_4}$: 0.94 (d, J=7 Hz)6H, 1.22(t, J=7 Hz)6H, 2.04–2.44(m)1H, 2.64 (d, J=7 Hz)2H, 4.16(q, J=7 Hz)4H, 5.90(t, J=7 Hz)1H.

In 20 g of ethanol were dissolved 8.8 g of the above diethyl isopropyl-(3,3-dichloroallyl)malonate and a solution of 6.4 g of potassium hydroxide in 10 g of water was added to the above ethanol solution. The mixture was refluxed overnight. Then, the reaction mixture was distilled to remove the ethanol and a sufficient amount of dilute hydrochloric acid was added to make the residue acidic. The residue was extracted with diethyl ether and the ethereal layer was dried over anhydrous magnesium sulfate and distilled to remove the low-boiling fraction. By this procedure there was obtained a mixture of isopropyl-(3,3-dichloroallyl)malonic acid and morbethyl isopropyl-(3,3-dichloroallyl)malonate. This mixture was subjected to decarboxylation reaction at 180° to 230° C. under a reduced pressure of 35 to 60 mmHg, whereupon 6.0 g of a mixture of α-(3,3-dichloroallyl) isovaleric acid and ethyl α-(3,3-dichloroallyl)isovalerate was obtained. In 20 g of ethanol were dissolved 6.0 g of the above decarboxylated mixture and a solution of 1.2 g of sodium hydroxide in 10 g of water was added to the above solution. The mixture was refluxed for 4 hours, after which the ethanol was distilled off. The residue was made acidic with dilute hydrochloric acid and extracted with diethyl ether. The ethereal layer was dried over anhydrous magnesium sulfate and distilled to remove the low-boiling fraction. By the above procedure there were obtained 4.2 g of α-(3,3-dichloroallyl)isovaleric acid, the NMR spectrum of which appears below [yield: 70% based on diethyl isopropyl-(3,3-dichloroallyl)malonate].

NMR spectrum (60 MHz) $\delta_{HMS}^{CCl_4}$: 1.01(d, J=7 Hz)6H, 1.67–2.67(m)4H, 5.94(t, J=7 Hz)1H.

To 2.1 g of α-(3,3-dichloroallyl)isovaleric acid were added 3.0 g of thionyl chloride, as well as 10 g of benzene, and the mixture was refluxed for 5 hours. Then, the reaction mixture was distilled to remove the low-boiling fraction. By this procedure there was obtained α-(3,3-dichloroallyl)isovaleroyl chloride. This chloride was dissolved in 30 g of dry benzene, followed by the addition of 2.0 g of 3-phenoxybenzyl alcohol. Then, 2.0 g of pyridine were added added dropwise and the mixture was stirred at room temperature overnight. The reaction mixture was then diluted with diethyl ether, washed with dilute hydrochloric acid and water, dried over anhydrous magnesium sulfate and distilled to remove the low-boiling fraction. The residual viscous oil was purified by column chromatography to recover 3.1 g of 3-phenoxybenzyl α-(3,3-dichloroallyl)isovalerate (Compound [5]) having the following properties [yield: 79% based on α-(3,3-dichloroallyl)isovaleric acid].

NMR spectrum (60 MHz) $\delta_{TMS}^{CDCl_3}$: 0.94(d, J=7 Hz)6H, 1.65–2.66(m)4H, 5.14(s)2H, 5.87(t, J=7 Hz)1H, 6.83–7.60(m)9H.

Elemental analysis (Calcd. in parentheses): C% 64.20(64.13) H% 5.58(5.64).

SYNTHESIS EXAMPLES 4 & 5

The procedure of Synthesis Example 3 was repeated, except that 2.3 g of α-cyano-3-phenoxybenzyl alcohol or 2.3 g of α-ethynyl-3-phenoxybenzyl alcohol, respectively, were used in lieu of 2.0 g of 3-phenoxybenzyl alcohol. By these procedures there were obtained the corresponding α-(3,3-dichloroallyl) isovaleric acid esters (Compound [6] and Compound [7], respectively. The yields, NMR spectra and elemental analyses of these esters are shown below.

Compound [6]: yield 3.5 g (84%)
NMR spectrum (60 MHz) $\delta_{TMS}^{CDCl_3}$: 0.78–1.05(m)6H, 1.63–2.52(m)4H, 5.60–5.94(m)1H, 6.38(s)1H, 6.85–7.55(m)9H.

Elemental analysis (Calcd. in parentheses): C% 63.09 (63.17) H% 4.95 (5.06).

Compound [7]: yield 3.0 g (72%)
NMR spectrum (60 MHz) $\delta_{TMS}^{CDCl_3}$: 0.81–1.05(m)6H, 1.62–2.55(m)4H, 2.63(d, J=2 Hz)1H, 5.67–5.98(m)1H, 6.47(d, J=2 Hz)1H, 6.87–7.55(m)9H.

Elemental analysis (Calcd. in parentheses): C% 66.31(66.20) H% 5.38(5.31).

SYNTHESIS EXAMPLE 6

In 100 g of methanol were dissolved 10.0 g of ethyl α-allylisovalerate (general formula [XI] wherein R=—CH$_2$CH$_3$) and, under cooling at −20° ~ −10° C. and stirring, ozone gas was bubbled into the solution for 8 hours. Then, at room temperature, the reaction mixture was added to 100 g of dimethyl sulfide and the mixture was stirred at that temperature overnight. The reaction mixture was then distilled under reduced pressure to remove the low-boiling fraction and the residue was diluted with 50 g of diethyl ether. Following the addition of 4 g of anhydrous calcium chloride, hydrogen chloride gas was bubbled into the mixture at room temperature for 10 minutes. Then, 5 g of anhydrous potassium carbonate were added and the mixture was thoroughly stirred. The diethyl ether solution was taken, washed with water, dried over anhydrous magnesium sulfate and distilled under reduced pressure to remove the low-boiling fraction. By the above procedure there were obtained 9.0 g of ethyl 2-isopropyl-3-formyl-propionate (general formula [XII] wherein R=—CH$_2$CH$_3$) yield: 89% based on ethyl α-allylisovalerate; the NMR spectrum of the aldehyde (60 MHz) $\delta_{HMS}^{CDCl_3}$: 9.74].

In 240 g of methylene chloride were dissolved 12.5 g of carbon tetrabromide, followed by the addition of 19.8 g of triphenylphosphine. The mixture was thoroughly stirred. To this mixed solution were added 5.0 g of the ethyl 2-isopropyl-3-formyl-propionate prepared above and the mixture was stirred at room temperature overnight. Thereafter, the low-boiling fraction was distilled off under reduced pressure and the residue was stirred well with diethyl ether and water. The diethyl ether layer was taken and distilled under reduced pressure to remove the low-boiling fraction. To the residue was added petroleum ether and, after thorough stirring, the petroleum ether solution was taken and further distilled under reduced pressure to remove the low-boiling fraction. The resultant oily residue was purified by distillation under reduced pressure. By the above procedure there were obtained 4.6 g of ethyl α-(3,3-dibromoallyl)isovalerate [yield: 48% based on ethyl 2-isopropyl-3-formyl-propionate].

NMR spectrum (60 MHz) $\delta_{HMS}^{CDCl_3}$: 0.88(d, J=6.5 Hz)6H, 1.20(t, J=7 Hz)3H, 1.65–2.38(m)4H, 4.09(q, J=7 Hz)2H, 6.35(t, J=7 Hz)1H.

In a mixture of 7 g of water and 20 g of ethanol were dissolved 1.1 g of sodium hydroxide and 4.6 of the ethyl α-(3.3-dibromoallyl)isovalerate obtained above were added to the above solution. The mixture was stirred at room temperature overnight and, then, refluxed for 3 hours. The reaction mixture was then distilled to remove the ethanol and the residue was made acidic by the addition of dilute hydrochloric acid and extracted with diethyl ether. The ethereal layer was dried over anhydrous magnesium sulfate and the low-boiling fraction was distilled off. By the above procedure there were obtained 3.7 g of α-(3,3-dibromoallyl)isovaleric acid, the NMR spectrum of which is shown below [yield: 88% based on ethyl α-(3,3-dibromoallyl)isovalerate].

NMR spectrum (60 MHz) $\delta_{HMS}^{CDCl_3}$: 0.92(d, J=6.5 Hz)6H, 1.67–2.42(m)4H, 6.39(t, J=7 Hz) 1H, 10.63(s)1H.

In 20 g of benzene were dissolved 2.0 g of α-(3,3-dibromoallyl) isovaleric acid, followed by the addition of 4.7 g of thionyl chloride and 2 drops of N,N-dimethylformamide. The mixture was refluxed overnight and, then, distilled to remove the low-boiling fraction. As the residue there was obtained α-(3,3-dibromoallyl)isovaleroyl chloride. This α-(3,3-dibromoallyl) isovaleroyl chloride was dissolved in 30 g of dry benzene and 1.5 g of α-ethynyl-3-phenoxybenzyl alcohol were added. This was further followed by the dropwise addition of 1.6 g of pyridine and the mixture was stirred at room temperature overnight. Thereafter, the reaction mixture was further stirred at 40°–50° C. for 2 hours, after which it was diluted with diethyl ether, washed with dilute hydrochloric acid and water, dried over anhydrous magnesium sulfate and distilled to remove the low-boiling fraction. The resultant viscous oil was purified by column chromatography to recover 2.0 g of α-ethynyl-3-phenoxybenzyl α-(3,3-dibromoallyl)isovalerate (Compound [10]) which was shown to have the properties indicated below [yield: 59% based on α-(3,3-dibromoallyl)isovaleric acid].

NMR spectrum (60 MHz) $\delta_{HMS}^{CDCl_3}$: 0.74–1.03(m)6H, 1.60–2.43(m)4H, 2.53–2.63(m)1H, 6.12–6.50(m)2H, 6.84–7.50(m).

Elemental analysis (Calcd. in parentheses): C% 54.66 (54.57) H% 4.40(4.38).

SYNTHESIS EXAMPLES 7 & 8

The procedure described in Synthesis Example 6 was followed except that 1.4 g of 3-phenoxybenzyl alcohol or 1.5 g of α-cyano-3-phenoxybenzyl alcohol, respectively, were used in lieu of 1.5 g of α-ethynyl-3-phenoxybenzyl alcohol. By these procedures there were obtained the corresponding α-(3,3-dibromoallyl)isovaleric acid esters (Compound [8] and Compound [9]), respectively. The yields, NMR spectra and elemental analyses of these esters are given below.

Compound [8]: yield 2.6 g (81%)
NMR spectrum (60 MHz) $\delta_{TMS}^{CDCl_3}$: 0.91(d, J=6.5H)6H, 1.65–2.50(m)4H, 5.09(s)2H, 6.35(t, J=7 Hz)1H, 6.87–7.50(m)9H.

Elemental analysis (Calcd. in parentheses): C% 52.18(52.31) H% 4.55(4.60).

Compound [9]: yield 2.2 g (65%)
Elemental analysis (Calcd. in parentheses): C% 51.97(52.10) H% 4.12(4.17).

SYNTHESIS EXAMPLE 9

A pressure-resistant tubular reactor was charged with a mixture of 20.0 g of ethyl 3,3-dimethyl-4-pentenate, 200 g of chloroform and 1.0 g of t-butyl perbenzoate and, after the tube was sealed, the contents were heated at 120° C. for 20 hours. Then, the reaction mixture was distilled to remove the low-boiling fraction and further subjected to distillation under reduced pressure. By the above procedure there were obtained 27.2 g of ethyl β-(3,3,3-trichloropropyl)isovalerate(ethyl 6,6,6-trichloro-3,3-dimethylhexanoate) (yield: 77%).

b.p. 90°–92° C./0.6 mmHg

NMR spectrum (60 MHz) $\delta_{TMS}^{CDCl_3}$: 1.07(s), 1.26(t, J=7 Hz)9H; 1.67–2.03(m)2H; 2.24(s)2H; 2.60–2.95(m)2H; 4.17(q, J=7 Hz)2H.

In 50 g of ethanol were dissolved 2.5 g of sodium metal and 20.0 g of the above ethyl β-(3,3,3-trichloropropyl)isovalerate were added to the solution. The mixture was refluxed for 8 hours. The reaction mixture was neutralized with a solution of hydrogen chloride in dry ethanol and concentrated to about one-twentieth of its original volume. To this concentrate were added 100 g of ice-water and the mixture was extracted with diethyl ether. The ethereal layer was dried over anhydrous magnesium sulfate and distilled to remove the low-boiling fraction. By the above procedure there were obtained 13.7 g of ethyl β-(3,3-dichloroallyl)isovalerate (ethyl 6,6-dichloro-3,3-dimethyl-5-hexenoate), the NMR spectrum of which is given below (yield: 79%).

NMR spectrum (60 MHz) $\delta_{HMS}^{CCl_4}$: 0.99(s)6H, 1.20(t, J=7.5 Hz)3H, 2.09–2.35(m)4H, 4.07 (q, J=7.5 Hz)2H, 5.94(t, J=7.5 Hz)1H.

To a solution of 2.2 g of sodium hydroxide in 15 g of water were added 10.0 g of the above ethyl β-(3,3-dichloroallyl)isovalerate as well as 20 g of ethanol, and the mixture was refluxed for 4 hours. The reaction mixture was distilled to remove the ethanol, made acidic with aqueous hydrogen chloride and extracted with diethyl ether. The ethereal layer was dried over anhydrous magnesium sulfate and distilled to remove the low-boiling fraction. By the above procedure there were obtained 8.2 g of β-(3,3-dichloroallyl)isovaleric acid (6,6-dichloro-3,3-dimethyl-5-hexenoic acid), the NMR spectrum of which is given below (yield: 93%).

NMR spectrum (60 MHz) $\delta_{HMS}^{CCl_4}$: 1.04(s)6H, 2.14–2.34(m)4H, 5.94(t, J=7.5 Hz)1H.

To 2.1 g of β-(3,3-dichloroallyl)isovaleric acid were added 3.0 g of thionyl chloride and 10 g of benzene, and the mixture was refluxed for 5 hours. The reaction mixture was then distilled to remove the low-boiling fraction and recover β-(3,3-dichloroallyl)isovaleroyl chloride as the residue. This β-(3,3-dichloroallyl)isovaleroyl chloride was dissolved in 30 g of dry benzene and 2.0 g of 3-phenoxybenzyl alcohol were added to the solution. This was further followed by the dropwise addition of 1.6 g of pyridine and the mixture was stirred at room temperature overnight. Thereafter, the reaction mixture was diluted with diethyl ether, washed with dilute aqueous hydrogen chloride and water, dried over anhydrous magnesium sulfate and distilled to remove the low-boiling fraction. The resulting oily residue was purified by column chromatography to obtain 2.8 g of 3-phenoxybenzyl β-(3,3-dichloroallyl)isovalerate (Compound [11] having the following properties [yield: 71% based on β-(3,3-dichloroallyl)isovaleric acid].

NMR spectrum (60 MHz) $\delta_{HMS}^{CCl_4}$: 0.93(s)6H, 2.03–2.23(m)4H, 4.98(s)2H, 5.88 (t, J=7.5 Hz) 1H, 6.76–7.50(m)9H.

Elemental analysis (Calcd. in parentheses): C% 64.08(64.13) H% 5.60(5.64).

SYNTHESIS EXAMPLES 10 & 11

The procedure described in Synthesis Example 9 was repeated except that 2.2 g of α-cyano-3-phenoxybenzyl alcohol or 2.2 g of α-ethynyl-3-phenoxybenzyl alcohol, respectively, were used in lieu of 2.0 g of 3-phenoxybenzyl alcohol. By these procedures there were obtained the corresponding esters of β-(3,3-dichloroallyl)isovaleric acid (Compound [12] and Compound [13], respectively. The yields, NMR spectra and elemental analyses of these esters are given below.

Compound [12]: yield 3.4 g (81%)

NMR spectrum (60 MHz) $\delta_{TMS}^{CDCl_3}$: 1.01(s)6H; 2.19(d, J=8 Hz), 2.30(s)4H; 5.89(t, J=8 Hz)1H; 6.38(s)1H; 6.90–7.50(m)9H.

Elemental analysis (Calcd. in parentheses): C% 62.98(63.17) H% 5.06(5.06).

Compound [13]: yield 3.3 g (79%)

NMR spectrum (60 MHz) $\delta_{TMS}^{CDCl_3}$: 0.96(s)6H, 2.07–2.28(m)4H, 2.53(d, J=2 Hz)1H, 5.87(t, J=8 Hz)1H, 6.44(d, J=2 Hz)1H, 6.83–7.50(m)9H Elemental analysis (Calcd. in parentheses): C% 66.05(66.20) H% 5.19(5.31).

SYNTHESIS EXAMPLE 12

In 150 g of benzene were dissolved 62.7 g of 3,3-dimethyl-4-(2,2-dichlorovinyl)-4-butanolide and, at room temperature, hydrogen chloride gas was bubbled into the solution for one hour. Then, 3.0 g of zinc chloride were added and the mixture was refluxed. While the introduction of hydrogen chloride gas was continued, 107.0 g of thionyl chloride were added dropwise over a period of one hour. The mixture was further heated at that temperature for 4 hours, after which time the excess thionyl chloride and benzene were distilled off under reduced pressure. The residue was subjected to distillation under reduced pressure to recover 49.1 g of 3,3-dimethyl-4,6,6-trichloro-5-hexenoyl chloride which was shown to have the following properties [yield: 62%].

b.p. 79°–81° C./0.65 mmHg

NMR spectrum (60 MHz) $\delta_{HMS}^{CCl_4}$: 1.14(s)3H, 1.17(s)3H, 2.87(d, J=17 Hz)1H, 3.22(d, J=17 Hz)1H, 4.83(d, J=10.5 Hz)1H, 6.04(d, J=10.5 Hz)1H.

In 30 g of dry benzene were dissolved 2.6 g of 4,6,6-trichloro-3,3-dimethyl-5-hexenoyl chloride and 2.0 g of 3-phenoxybenzyl alcohol were added to the solution. This was followed by the dropwise addition of 2.4 g of pyridine and the mixture was stirred at room temperature overnight. The reaction mixture was then diluted with diethyl ether, washed with dilute aqueous hydrogen chloride and water, dried over anhydrous magnesium sulfate and distilled to remove the low-boiling fraction. The residual viscous oil was purified by column chromatography. By the above procedure there were obtained 3.9 g of 3-phenoxybenzyl β-(1,3,3-trichloroallyl)isovalerate (3-phenoxybenzyl 4,6,6-trichloro-3,3-dimethyl-5-hexenoate, Compound [17]) the NMR spectrum and elemental analysis of which are given below [yield: 91%].

NMR spectrum (60 MHz) $\delta_{HMS}^{CCl_4}$: 1.03(s)6H, 2.18(d, J=15 Hz)1H, 2.52(d, J=15 Hz)1H, 4.87 (d, J=10.5 Hz)1H, 5.02(s)2H, 6.02(d, J=10.5 Hz)1H, 6.80–7.50(m)9 H.

Elemental analysis (Calcd. in parentheses): C% 58.85(58.97) H% 5.02 (4.97).

SYNTHESIS EXAMPLES 13 & 14

The procedure described in Synthesis Example 12 was repeated except that 2.3 g of α-cyano-3-phenoxybenzyl alcohol or 2.3 g of α-ethynyl-3-phenoxybenzyl alcohol, respectively, were used in lieu of 2.0 g of 3-phenoxybenzyl alcohol. By the above procedures there were obtained the corresponding esters of β-(1,3,3-trichloroallyl)isovaleric acid (Compound [18] and Compound [19]), respectively. The yields, NMR spectra and elemental analysis of these esters are as follows:

Compound [18]: yield 3.8 g (84%)

NME spectrum (60 MHz) $\delta_{TMS}^{CDCl_3}$: 1.08(s)6H; 2.33(db, J=15 Hz), 2.66(bd, J=15 Hz)2H; 4.80(d, J=10.5 Hz)1H; 6.02(d, J=10.5 Hz)1H; 6.36(s)1H; 6.92–7.58(m)9H.

Elemental analysis (Calcd. in parentheses): C% 58.45(58.36) H% 4.41(4.45).

Compound [19]: yield 3.6 g (80%)

NMR spectrum (100 MHz) $\delta_{TMS}^{CDCl_3}$: 0.94(s)6H; 2.11(d, J=15 Hz), 2.14(d, J=15 Hz), 2.38 (d, J=15 Hz), 2.41(d, J=15 Hz), 2.45(d, J=2 Hz)3H; 4.69(d, J=11 Hz), 4.72(d, J=11 Hz)1H; 5.86(d, J=11 Hz)1H; 6.30(d, J=2 Hz)1H; 6.70–7.25(m)9H.

Elemental analysis (Calcd. in parentheses): C% 61.25 (61.14) H% 4.60(4.68).

TEST EXAMPLE 1

Mortality test against houseflies by topical application method

Each test compound was accurately weighed and a 1% solution and a 0.1% solution of the sample in acetone were prepared. A 1 μl portion of either of the above solutions was micropipetted onto the thoracic dorsal part of each female adult housefly (*Musca domestica*) under ether anaesthesia and the fly was released in a high-walled dish together with feed. The dish was covered with a metal-wire net and maintained at 25° C. After 24 hours, the test flies were inspected for deaths and the mortality (%) was calculated. The results are set forth in Table 1. Thirty test flies were used per concentration group.

TABLE 1

| Test Compound No. | Mortality (%) | |
|---|---|---|
| | 10 μg/fly | 1 μg/fly |
| [1] | 100 | 100 |
| [2] | 100 | 100 |
| [5] | 100 | 100 |
| [6] | 100 | 100 |
| [7] | 100 | 90 |
| [8] | 100 | 100 |
| [9] | 100 | 100 |
| [10] | 100 | 100 |
| [11] | 100 | 100 |
| [12] | 100 | 100 |
| [13] | 100 | 90 |
| [17] | 100 | 100 |
| [18] | 100 | — |
| [19] | 100 | — |
| Allethrin | 100 | 50 |
| 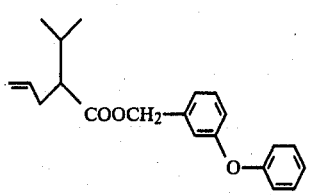 | 0 | 0 |
| 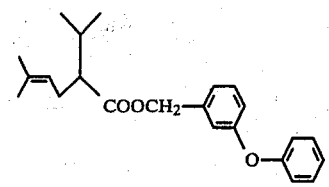 | — | 0 |

TEST EXAMPLE 2

Mortality test against green rice leafhoppers by topical application method

Each test compound was accurately weighed and an 0.1% solution in acetone was prepared. Female adults of green rice leafhopper (*Nephotettix cincticeps*) were anaesthetized with carbon dioxide gas and 0.5 μl of the above solution was micropipetted onto the thoracic abdominal part of each leafhopper. Then, the test leafhoppers were kept at 25° C. with access to rice plant seedlings. Each group comprised 15 green rice leafhoppers. After 24 hours, the leafhoppers were inspected for deaths and the mortality (%) was calculated for each compound. The results are set forth in Table 2.

TABLE 2

| Test Compound No. | Mortality (%) |
|---|---|
| [1] | Not less than 90% |
| [2] | " |
| [6] | " |
| [7] | " |
| [9] | " |
| [10] | " |
| [12] | " |
| [13] | " |
| 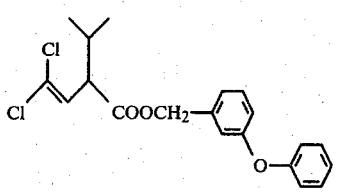 | 40% |

TEST EXAMPLE 3

Mortality test against cockroaches by topical application method

Each test compound was accurately weighed and made in a 1% solution in acetone. Then, 1 μl of the above solution was micropipetted onto the abdominal part of each female cockroach (*Blattella germanica*) under ether anaesthesia. The roaches were released in a high-walled dish together with feed and, after the disk was covered with a metal wire net, same was maintained at 25° C. Fifteen roaches per group were employed. After 24 hours, the test roaches were inspected for deaths and the mortality (%) for each group was calculated. The results are set forth in Table 3.

TABLE 3

| Test Compound No. | Mortality (%) |
|---|---|
| [1] | 100 |
| [2] | 80 |
| [6] | 100 |
| [7] | 80 |

TEST EXAMPLE 4

Light stability test

Into 2.0 ml of acetone were dissolved 80 mg of each test compound. A 5 μl portion of the solution was taken and spread on a glass plate (Micro Standard Cover Glass, 18 m/m No. 1, 200 pcs, Matsunami Glass Ind., Ltd.) and the acetone was evaporated. Then, a similar glass plate was superimposed on the above plate in such a manner that the test liquid was sandwitched. The specimen was exposed to direct sunlight at an atmospheric temperature of 12° C. for a predetermined exposure time. As an unexposed control, a similar specimen was covered with an aluminum foil. The test liquid was washed away with 1.0 ml of methanol containing 0.04% of dioctyl phthalate as an internal reference and high-speed liquid chromatography was carried out on the washings to determine the residual amount of the test compound. The percent residue (%) is shown in Table 4. The residue (%) was calculated with the value for the aluminum foil-covered control specimen as the standard.

TABLE 4

| Test Compound No. | Residue (%) Exposure time | |
|---|---|---|
| | 4 hrs. | 8 hrs. |
| [1] | 93 | 90 |
| [2] | 97 | 100 |
| [5] | 99 | 98 |
| [6] | 92 | 92 |
| [7] | 96 | 96 |
| [10] | 97 | 97 |
| [11] | 100 | 96 |
| [12] | 92 | 90 |
| [13] | 100 | 100 |
| [17] | 100 | 100 |
| [18] | 98 | 97 |
| [19] | 97 | 92 |
| Allethrin | 35 | 17 |

TEST EXAMPLE 5

Hydrolysis resistance test

Into about 8 ml of acetone were dissolved 100 mg of each test compound and, then, 1.0 g of water was added to this solution to prepare a mixed solution. This mixed solution was refluxed for 2 days. After concentration to about one half of the original volume and with the addition of dioctyl phthalate as an internal reference, the residual amount of the compound was determined by high-speed liquid chromatography. The residue (%) was then calculated. The results are set forth in Table 5.

TABLE 5

| Test Compound No. | Residue (%) |
|---|---|
| [2] | more than 90 |
| [6] | " |
| [7] | " |
| [11] | " |
| [12] | " |
| [18] | " |

TEST EXAMPLE 6

Fish toxicity test

To 5 l of water were added 250 mg of sorpol SM-200 (registered trademark, Toho Chemical Co., Ltd.) or Tween-20 (commercial product) as an emulsifier (surfactant) as well as 2.5 ml of an acetone solution containing one of the test compounds in a predetermined concentration. The mixture was stirred well to prepare a test water. Ten female guppies from 3 to 4 months of age were released into the test water and maintained at 25° C. The concentration of the test compound at which 90% or more of the guppies were killed during the ensuring 48 hours was determined. (This concentration is referred to as $LC_{90}$). The results are set forth in Table 6.

TABLE 6

| Test Compound No. | $LC_{90}$ |
|---|---|
| [2] | Not less than 10 ppm |
| [5] | " |
| [7] | " |
| [8] | " |
| [10] | " |
| [11] | " |
| [12] | " |
| [13] | " |
| [17] | " |
| [18] | " |
| [19] | " |
| Allethrin | Not more than 0.5 ppm |
| Permethrin | " |
| Fenvalerate | " |

FORMULATION EXAMPLE 1

0.2 part of each of Compounds [1], [2], [5] to [13] and [17] was prepared and 0.8 part of piperonyl butoxide was added to each of them. To this mixture was added a sufficient amount of kerosene to make 100 parts, followed by stirring. By this procedure there was obtained an oil preparation of each Compound.

FORMULATION EXAMPLE 2

To 0.1 part of each of Compounds [1] to [17] was added 0.1 part of resmethrin, followed by the addition of a sufficient amount of kerosene to make 100 parts. The mixture was stirred to obtain an oil preparation of each compound.

FORMULATION EXAMPLE 3

To 0.1 part of each of Compounds [1] to [28] was added 0.08 part of permethrin, followed by the addition of a sufficient amount of kerosene to make 100 parts. The mixture was stirred to obtain an oil preparation of each compound.

FORMULATION EXAMPLE 4

To 0.2 part of each of Compounds [1], [2], [5] to [13] and [17] to [19] was added 0.2 part of 2-isopropoxyphenyl N-methylcarbamate and 5 parts of xylene. The composition was dissolved in a sufficient amount of kerosene to make 100 parts. In the above manner, an oil preparation of each compound was obtained.

FORMULATION EXAMPLE 5

To 30 parts of each of Compounds [1], [2], [5] to [13] and [17] to [19] was added 50 parts of xylene and 20 parts of Sorpol SM-200 (a surfactant, trademark of Toho Chemical Co., Ltd.). The mixture was stirred well and dissolved to obtain a 30% emulsifiable concentrate.

FORMULATION EXAMPLE 6

To 20 parts of each of Compounds [1], [2], [5] to [9] and [11] to [13] were added 20 parts of O,O-dimethyl-O-4-cyanophenyl phosphorothioate [Thianox, trademark of Sumitomo Chemical Co., Ltd.], 20 parts of Sorpol SM-200 (a surfactant, trademark of Toho Chemical Co., Ltd.) and 40 parts of xylene. The mixture was stirred well to effect dissolution, whereby an emulsifiable concentrate of each compound was obtained.

FORMULATION EXAMPLE 7

To 20 parts of each of Compounds [1], [2], [5] to [13], [17] to [19] and [21] were added 5 parts of Sorpol SM-200 (a surfactant, trademark of Toho Chemical Co., Ltd.), followed by thorough mixing. With the addition of 75 parts of 300-mesh talc, the mixture was thoroughly stirred in a triturator. By the above procedure there was obtained a wettable powder of each compound.

FORMULATION EXAMPLE 8

To 15 parts of each of Compounds [1], [2] and [5] to [13] were added 15 parts of 1-naphthyl N-methylcarbamate and 5 parts of Sorpol SM-200 (a surfactant, trademark of Toho Chemical Co., Ltd.), followed by thorough mixing. With the addition of 65 parts of 300-mesh talc, the mixture was thoroughly stirred in a triturator to obtain a wettable powder of each compound.

FORMULATION EXAMPLE 9

To one part of each of Compounds [1], [2], [5] to [13] and [17] to [20] were added 5 parts of piperonyl butoxide and the mixture was dissolved in 20 parts of acetone. With the addition of 94 parts of 300-mesh diatomaceous earth, the mixture was stirred well and mixed in a triturator and the acetone was evaporated off. By the above procedure there was obtained a powder containing each compound.

FORMULATION EXAMPLE 10

To 0.4 part of each of Compounds [1] to [19] was added 0.1 part of resmethrin, 1.5 parts of octachlorodipropyl ether and 28 parts of refined kerosene. The solution thus obtained was dispensed into aerosol containers and, after the valve was attached, each container was filled with 70 parts of propellant (liquefied petroleum gas). By this procedure there was obtained an aerosol preparation of each compound.

FORMULATION EXAMPLE 11

To 0.3 part of each of Compounds [1], [2] and [5] to [13] was added 0.3 part of DDVP and the mixture was dissolved in a mixture of xylene and refined kerosene to make a total of 15 parts. Each solution was dispensed into aerosol containers and, after the valve was attached, each container was filled with 85 parts of a propellant (liquefied petroleum gas) through the filling valve. By the above procedure there was obtained an aerosol preparation of each compound.

FORMULATION EXAMPLE 12

To 0.5 part of each of Compounds [1] to [13] was added 0.5 part of BHT and 99.0 parts of mosquito incense coil materials including pyrethrum marc, sawdust, starch, etc. The mixture was evenly blended and processed into a mosquito coil in the manner conventional, per se.

FORMULATION EXAMPLE 13

To 0.05 g of each of Compounds [1], [2], [5], [8], [10] and [11] was added 0.02 g of furamethrin, 0.15 g of piperonyl butoxide and 0.1 g of EHT and the mixture was dissolved in an appropriate amount of chloroform. This solution was adsorbed uniformly on the surface of an asbestos mat having a size of 2.5 cm × 1.5 cm and a thickness of 0.3 mm, and another asbestos mat of the same size and thickness was superimposed on the treated surface. By this procedure there was obtained a fibrous fumigation pesticidal composition (mat) for heating on a hot plate.

UTILITY EXAMPLE 1

The emulsifiable concentrate prepared from Compounds [1], [2], [6], [7], [9], [10], [12] and [13] in Formulation Example 5 were each diluted 300-fold with water. Then, each of the dilutions was sprayed over rice seedlings 25 days after sowing at the rate of 10 ml/pot. The pot was covered with a wire-net and 15 green rice leafhoppers were released under the net. After 24 hours, the leafhoppers were examined for deaths. The mortality (%) was not less than 90% for each of Compounds [1], [2], [6], [7], [9], [10], [12] and [13].

UTILITY EXAMPLE 2

By the settling mist method, a mortality test against houseflies (*Musca domestica*) was carried out using the oil preparations obtained according to Formulation Example 1 from Compounds [1], [2], [5] to [11] to [17]. After 24 hours, the flies were examined for deaths. The mortality (%) was not less than 90% for each of Compounds [1], [2], [5] to [11] to [17].

UTILITY EXAMPLE 3

By the settling mist method, a mortality test against houseflies was carried out using the oil preparations made in Formulation Example 2 from Compounds [1], [2], [5] to [11] and [17]. After 24 hours, the flies were examined for deaths. The mortality (%) was not less than 90% for each of Compounds [1], [2], [5] to [11] and [17].

UTILITY EXAMPLE 4

By the settling mist method, a mortality test against house-flies was carried out using the oil preparations obtained in Formulation Example 3 from Compounds [1], [2], [5] to [11] and [17]. After 24 hours, the flies were examined for deaths. The mortality (%) was not less than 90% for each of Compounds [1], [2], [5] to [11] and [17].

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. An insecticidal composition comprising (i) an insecticidally effective amount of an isovalerate having the structural formula:

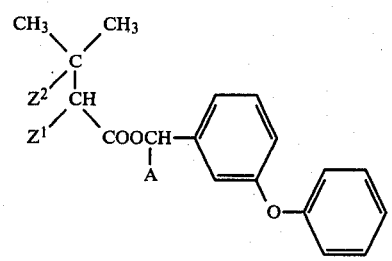

wherein $Z^1$ is a member selected from the group consisting of hydrogen and

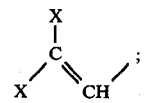

$Z^2$ is a member selected from the group consisting of

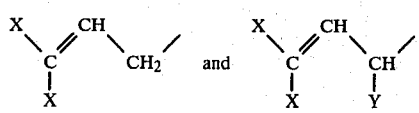

when $Z^1$ is hydrogen, and hydrogen when $Z^1$ is

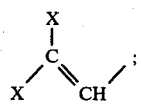

A, when $Z^1$ is

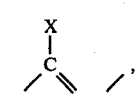

is a member selected from the group consisting of cyano and ethynyl, and when $Z^1$ is hydrogen, is a member selected from the group consisting of hydrogen, cyano and ethynyl; and X and Y which may be the same or different are each a member selected from the group consisting of chlorine and bromine, and (ii) an inert carrier therefor.

2. The insecticidal composition as defined by claim 1, wherein the isovalerate (i) has the structural formula:

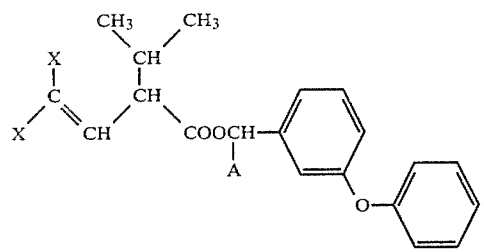

wherein A is a member selected from the group consisting of cyano and ethynyl, and each X, which may be the same or different, is selected from the group consisting of chlorine and bromine.

3. The insecticidal composition as defined by claim 2, wherein A is cyano.

4. The insecticidal composition as defined by claim 2, wherein A is ethynyl.

5. The insecticidal composition as defined by claim 1, wherein the isovalerate (i) has the structural formula:

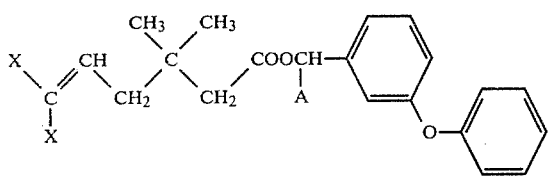

wherein A is selected from the group consisting of hydrogen, cyano and ethynyl, and each X, which may be the same or different, is selected from the group consisting of chlorine and bromine.

6. The insecticidal composition as defined by claim 5, wherein A is hydrogen.

7. The insecticidal composition as defined by claim 5, wherein A is cyano.

8. The insecticidal composition as defined by claim 5, wherein A is ethynyl.

9. The insecticidal composition as defined by claim 1, wherein the isovalerate (i) has the structural formula:

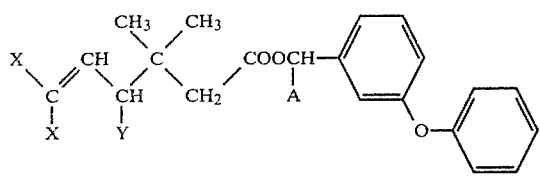

wherein A is selected from the group consisting of hydrogen, cyano and ethynyl, and each X and Y, which may be the same or different, is selected from the group consisting of chlorine and bromine.

10. The insecticidal composition as defined by claim 9, wherein A is hydrogen.

11. The insecticidal composition as defined by claim 9, wherein A is cyano.

12. The insecticidal composition as defined by claim 9, wherein A is ethynyl.

13. The insecticidal composition as defined by claim 1, wherein the isovalerate (i) is α-cyano-3-phenoxybenzyl α-(2,2-dichlorovinyl)isovalerate.

14. The insecticidal composition as defined by claim 1, wherein the isovalerate (i) is α-ethynyl-3-phenoxybenzyl α-(2,2-dichlorovinyl)isovalerate.

15. The insecticidal composition as defined by claim 1, formulated in the form of a liquid solution.

16. The insecticidal composition as defined by claim 1, formulated in the form of a wettable powder.

17. The insecticidal composition as defined by claim 1, formulated in the form of an emulsifiable concentrate.

18. The insecticidal composition as defined by claim 1, formulated in the form of a liquid suspension.

19. The insecticidal composition as defined by claim 1, formulated in the form of a dust.

20. The insecticidal composition as defined by claim 1, formulated in the form of a powder.

21. The insecticidal composition as defined by claim 1, formulated in aerosol form.

22. The insecticidal composition as defined by claim 1, formulated in granular form.

23. The insecticidal composition as defined by claim 1, formulated in fumigant form.

24. The insecticidal composition as defined by claim 1, formulated in capsular form.

25. The insecticidal composition as defined by claim 1, formulated as a coating composition.

26. The insecticidal composition as defined by claim 1, further comprising a surfactant.

27. The insecticidal composition as defined by claim 1, further comprising a dispersing agent.

28. The insecticidal composition as defined by claim 1, further comprising a foaming agent.

29. The insecticidal composition as defined by claim 1, wherein the inert carrier comprises a liquid.

30. The insecticidal composition as defined by claim 1, wherein the inert carrier comprises a gas.

31. The insecticidal composition as defined by claim 1, wherein the inert carrier comprises a solid.

32. The insecticidal composition as defined by claim 1, further comprising a second insecticidally effective pesticide.

33. The insecticidal composition as defined by claim 1, further comprising a member selected from the group consisting of a synergist, an antioxidant, and mixtures thereof.

34. The insecticidal composition as defined by claim 1, further comprising a member selected from the group consisting of an adhesive, a colorant, and mixtures thereof.

35. The insecticidal composition as defined by claim 1, wherein the isovalerate (i) is present in an amount of up to 95 weight percent.

36. The insecticidal composition as defined by claim 1, wherein the isovalerate (i) is present in an amount of from 0.1 to 90 weight percent.

37. The insecticidal composition as defined by claim 1, wherein the isovalerate (i) is present in an amount of from 0.001 to 10 weight percent.

38. A method for the control of insects, which comprises applying to the habitat of said insects an insecticidally effective amount of an isovalerate having the structural formula:

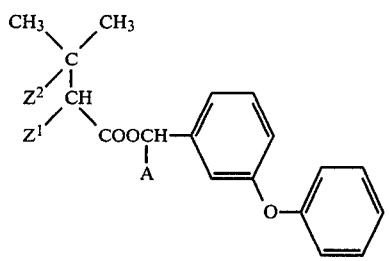

wherein $Z^1$ is a member selected from the group consisting of hydrogen and

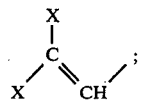

$Z^2$ is a member selected from the group consisting of

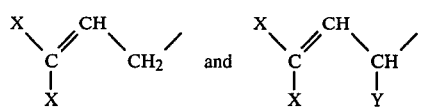

when $Z^1$ is hydrogen, and hydrogen when $Z^1$ is

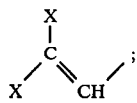

A, when $Z^1$ is

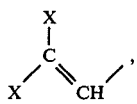

is a member selected from the group consisting of cyano and ethynyl, and when $Z^1$ is hydrogen, is a member selected from the group consisting of hydrogen, cyano and ethynyl; and X and Y which may be the same or different are each a member selected from the group consisting of chlorine and bromine.

39. The method as defined by claim 38, wherein the said insects comprise a pest selected from the group consisting of green rice leafhopper, plant hopper, rice stem borer, cabbage armyworm, diamond-back moth, owlet moth and underwing, common cabbage worm, Japanese giant silk moth, bean web worm, aphid, scale, mustard beetle, boll weevil, tobacco budworm, mite, housefly, mosquito, and cockroach.

40. The method as defined by claim 38, wherein the said insects comprise a pest selected from a family consisting of Tettigoniidae, Gryllidae, Gryllotalpidae, Blattidae, Reduviidae, Pyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae, Pulicidae, Tetranychidae and Dermanyssidae.

41. The method as defined by claim 38, wherein the isovalerate has the structural formula:

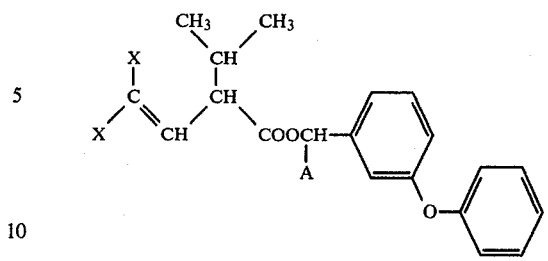

wherein A is a member selected from the group consisting of cyano and ethynyl, and each X, which may be the same or different, is selected from the group consisting of chlorine and bromine.

42. The method as defined by claim 41, wherein A is cyano.

43. The method as defined by claim 41, wherein A is ethynyl.

44. The method as defined by claim 38, wherein the isovalerate has the structural formula:

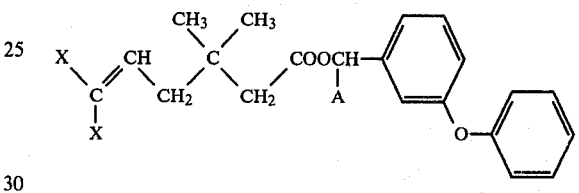

wherein A is selected from the group consisting of hydrogen, cyano and ethynyl, and each X, which may be the same or different, is selected from the group consisitng of chlorine and bromine.

45. The method as defined by claim 44, wherein A is hydrogen.

46. The method as defined by claim 44, wherein A is cyano.

47. The method as defined by claim 44, wherein A is ethynyl.

48. The method as defined by claim 38, wherein the isovalerate has the structural formula:

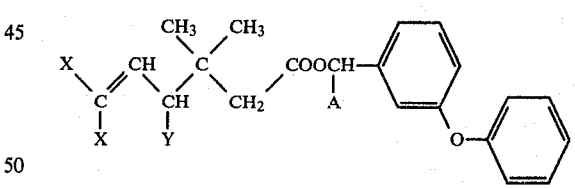

wherein A is selected from the group consisting of hydrogen, cyano and ethynyl, and each X and Y, which may be the same or different, is selected from the group consisting of chlorine and bromine.

49. The method as defined by claim 48, wherein A is hydrogen.

50. The method as defined by claim 48, wherein A is cyano.

51. The method as defined by claim 48, wherein A is ethynyl.

52. The method as defined by claim 38, wherein the isovalerate is α-cyano-3-phenoxybenzyl α-(2,2-dichlorovinyl) isovalerate.

53. The method as defined by claim 38, wherein the isovalerate is α-ethynyl-3-phenoxybenzyl α-(2,2-dichlorovinyl)isovalerate.

* * * * *